(12) United States Patent
Namdar

(10) Patent No.: US 12,016,870 B2
(45) Date of Patent: Jun. 25, 2024

(54) AGENTS FOR USE IN THE TREATMENT OF CARDIAC ARRHYTHMIA

(71) Applicant: Mehdi Namdar, Crans-Près-Céligny (CH)

(72) Inventor: Mehdi Namdar, Crans-Près-Céligny (CH)

( * ) Notice: Subject to any disclaimer, the term of this patent is extended or adjusted under 35 U.S.C. 154(b) by 405 days.

(21) Appl. No.: 17/281,276

(22) PCT Filed: Sep. 30, 2019

(86) PCT No.: PCT/EP2019/076455
§ 371 (c)(1),
(2) Date: Mar. 30, 2021

(87) PCT Pub. No.: WO2020/070067
PCT Pub. Date: Apr. 9, 2020

(65) Prior Publication Data
US 2022/0000895 A1 Jan. 6, 2022

(30) Foreign Application Priority Data
Oct. 1, 2018 (EP) .................................. 18197893

(51) Int. Cl.
*A61K 31/7028* (2006.01)
*A61P 9/06* (2006.01)

(52) U.S. Cl.
CPC ............ *A61K 31/7028* (2013.01); *A61P 9/06* (2018.01)

(58) Field of Classification Search
None
See application file for complete search history.

(56) References Cited

U.S. PATENT DOCUMENTS

2002/0177563 A1   11/2002   Griffin et al.

FOREIGN PATENT DOCUMENTS

WO    WO 81/03175    11/1981

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Manolis, A. J., Rosei, E. A., Coca, A., Cifkova, R., Erdine, S. E., Kjeldsen, S., . . . & Mancia, G. (2012). Hypertension and atrial fibrillation: diagnostic approach, prevention and treatment. Journal of hypertension, 30(2), 239-252. (Year: 2012).*

Abdulmajeed, R. et al. "The effects of long chain polyunsaturated fatty acids on local activation properties in dogs vulnerable to atrial fibrillation" *Conf Proc IEEE Eng Med Biol Soc.*, 2014, pp. 1067-1070.
Desplantez, T. et al. "Cardiac connexins Cx43 and Cx45: formation of diverse gap junction channels with diverse electrical properties" *Pflugers Arch—Eur J Physiol.*, 2004, pp. 363-375, vol. 448.
Dumpis, M. A. et al. "Molecular-biological problems in the creation of drugs and study of the mechanism of their action; antiarrhythmic agents: classification, structure, mechanism of action (review)" Dec. 31, 1984, pp. 685-693, retrieved from the Internet: URL:https://link.springer.com/content/pdf/10.1007/BF00765014 [retrieved on Mar. 12, 2019].
Fancellu, L. et al. "Exploratory screening for Fabry's disease in young adults with cerebrovascular disorders in northern Sardinia" *BMC Neurology*, 2015, pp. 1-7, vol. 15, No. 256.
Grace, A. A. et al. "Systems biology and cardiac arrhythmias" *Lancet*, Oct. 27, 2012, pp. 1-21, vol. 380, No. 9852.
Lau, D. H. et al. "Epicardial Border Zone Overexpression of Skeletal Muscle Sodium Channel SkM1 Normalizes Activation, Preserves Conduction, and Suppresses Ventricular Arrhythmia; An In Silico, In Vivo, In Vitro Study" *Circulation*, Jan. 2009, pp. 19-27, vol. 119, No. 1.
Lu, J. et al. "Improving Cardiac Conduction With a Skeletal Muscle Sodium Channel by Gene and Cell Therapy" *J Cardiovasc Pharmacol.*, Jul. 2012, pp. 88-99, vol. 60, No. 1.
Lei, M. et al. "Modernized Classification of Cardiac Antiarrhythmic Drugs" *Circulation*, Oct. 23, 2018, pp. 1879-1896, vol. 138.
Namdar, M. "Electrocardiogramanges and Arrhythmia in Fabry Disease" *Frontiers in Cardiovascular Medicine*, Mar. 24, 2016, pp. 1-6, vol. 3, Article 7.
Nattel, S. et al. "Atrial Remodeling and Atrial Fibrillation; Mechanisms and Implications" *Circ Arrhythmia Electrophysiol*, Apr. 2008, pp. 62-73, vol. 1.
Pandey, M. K. et al. "An unexpected player in Gaucher disease: The multiple roles of complement in disease development" *Seminars in Immunology*, 2018, pp. 30-42, vol. 37.
Savelieva, I. et al. "Anti-arrhythmic drug therapy for atrial fibrillation: current anti-arrhythmic drugs, investigational agents, and innovative approaches" *Europace*, 2008, pp. 647-665, vol. 10.
Takenaga, M. et al. "Effect of a soluble pseudo-receptor on verotoxin 2-induced toxicity" *J Infect Chemother*, 2000, pp. 21-25, vol. 6, No. 1.
Written Opinion in International Application No. PCT/EP2019/076455, dated Jan. 3, 2020, pp. 1-10.
Fuster, V. et al. "ACC/AHA/ESC 2006 Guidelines for the Management of Patients with Atrial Fibrillation" *Circulation*, pp. e257-e354, 2006, vol. 114.
Nicolaou, K. C. et al. "Total synthesis of globotriaosylceramide (Gb$_3$) and lysoglobotriaosylceramide (IsyoGb$_3$)" *Carbohydrate Research*, 1990, pp. 177-191, vol. 202.

* cited by examiner

*Primary Examiner* — Dale R Miller
(74) *Attorney, Agent, or Firm* — SALIWANCHIK, LLOYD & EISENSCHENK

(57) ABSTRACT

The present invention relates to glycosphingolipids selected from a globotriaosylceramide, a glucosylceramide, a galactosylceramide, a lactosylceramide and a sphingosine derivative of those or a mixture thereof, formulations thereof for the prevention and/or treatment of cardiac arrhythmias, in particular atrial fibrillation.

16 Claims, 2 Drawing Sheets

* p < 0.0001 vs control
* p < 0.005 vs control

AGENTS FOR USE IN THE TREATMENT OF CARDIAC ARRHYTHMIA

CROSS-REFERENCE TO RELATED APPLICATION

This application is the U.S. national stage application of International Patent Application No. PCT/EP2019/076455, filed Sep. 30, 2019.

FIELD OF THE INVENTION

The present invention relates to agents for the treatment of cardiac arrhythmias based on re-entry mechanisms, in particular atrial fibrillation.

BACKGROUND OF THE INVENTION

A cardiac arrhythmia is an abnormal beating of the heart and should the heart rate be too fast or the heart beats in an irregular fashion, the heart's ability to pump blood can be compromised. Impaired blood flow to the brain can lead to lightheadedness or even loss of consciousness or death. The lightheadedness or loss of consciousness can last for a few seconds or a longer time. Patients with an arrhythmia may notice palpitations, a fast and/or irregular heartbeat, shortness of breath or may stay asymptomatic.

The vast majority of arrhythmias are based on re-entry-mechanisms and come along with structural as well as electrophysiological remodeling processes of the myocardium.

Atrial fibrillation (AF) is the most common sustained cardiac arrhythmia occurring in 1-2% of the general population with over 6 million Europeans suffering from paroxysmal or persistent AF. This arrhythmia is associated with a considerable morbidity, mortality and expenditure of health care resources, primarily caused by cardioembolic stroke and/or heart failure. Moreover, its prevalence is expected to at least double in the next 50 years as the population ages (Kirchhof et al., 2016, *Eur Heart J.*, 37(38):2893-2962; Go et al., 2001, *Jama*, 285:2370-5; Singh et al., 2010, *J Am Coll Cardiol*, 55:1569-76). Among the many risk factors that promote the development of AF, the most prominent are sex (more prevalent in males than females), old age (>60 years-old) and arterial hypertension. Arterial hypertension and aging lead to structural changes of the extracellular matrix (ECM) and enhanced AF vulnerability due to the altered myocardial substrate (Burstein et al., 2008, *J Am Coll Cardiol.*, 51:802-809). It has been repeatedly demonstrated that pulmonary vein (PV) ectopic activity is the main trigger of paroxysmal AF, involving both triggered activity and re-entry mechanisms due to shorter refractory periods as well as abrupt changes in myocyte fiber orientation (Chen et al., 2006, *J Cardiovasc Electrophysiol* 2006; 17:220-4; Haïssaguerre et al., 1998, *N Engl J Med*, 339:659-66). However, once AF is established, atrial ultrastructural as well as electrophysiological changes (electrical remodeling) come along with shortening of the atrial effective refractory period (by down-regulation of the L-type Ca++ inward current and up-regulation of inward rectifier K+ currents) giving rise to an increased stability and sustainability of AF (Daoud et al., 1996, *Circulation*, 94:1600-6). Nowadays, pulmonary vein (PV) isolation by means of radiofrequency ablation at or close to the junction between the PVs and the left atrium targeting sites with a high dominant frequency, is the treatment of choice for symptomatic AF refractory to at least one class I or III antiarrhythmic drug (Kirchhof et al. 2016 supra; Cheema et al., 2006, *J Cardiovasc Electrophysiol*, 17:1080-5; Lemola et al., 2005, *J Am Coll Cardiol*, 46:1060-6).

However, although very effective in maintaining long-term sinus rhythm in patients with paroxysmal AF (Aryana et al., 2008, *Pacing Clin Electrophysiol.*, 31(6):782-783), this technique still remains complex in paroxysmal forms eventually progressing to persistent AF, where mechanisms include both triggers for its onset as well as a substrate (remodeled left atrial tissue) for its maintenance. Accordingly, sites with a high dominant frequency are spread throughout the entire atria and sustained sinus rhythm, even if used in concert with currently available antiarrhythmic therapeutic options, remains a huge challenge. Furthermore, mechanisms and patterns involved in spontaneous initiation and above all termination of AF remain elusive.

The glycosphingolipid globotriaosylceramide (Gb3)

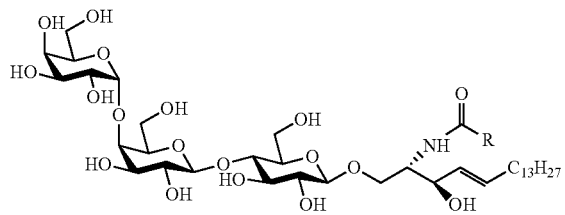

wherein R is selected from $C_{15}H_{31}$, $C_{19}H_{39}$, $C_{21}H_{43}$, $C_{23}H_{47}$ and $C_{23}H_{47}O$, depending on the isoforms and its deacetylated derivative (sphinganine) Lyso-Gb3

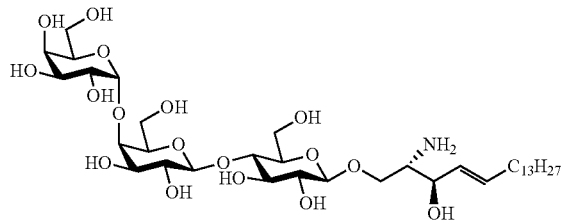

are known for their role on cardiac tissue, namely inducing endothelial dysfunction, diastolic dysfunction, right and left ventricule hypertropy, dilatation of the atrium, valvulopathies and micro- and macrofibrosis (Namdar et al, 2016, *Frontiers in Cardiovascular Medicine*, 3(7), 1-5). Further, in Fabry disease (FD), an X-linked (Xq22) systemic lysosomal storage disorder caused by subnormal or absent activity of the enzyme alpha-galactosidase A (a-Gal A), progressive accumulation of globotriaosylceramide (Gb3) in various organ systems including the heart, is associated, once the disease has developped, with arrhythmogenic effects (Namdar et al, 2016, *Frontiers in Cardiovascular Medicine*, supra). β-glycosylceramide (glucocerebroside, GC or GL1) is known in for its role in the development of Gaucher disease (Pandey et al., 2018, *Seminars in Immunology*, 37, 30-42).

Current methods used for suppression of AF (drugs or ablation) are all limited by some inefficacy, intolerance and/or toxicity. In fact, existing anti-arrhythmic drug approaches have limited effectiveness and are associated with risks of serious complications (Fuster et al, 2006, *Circulation*, 114:e257-e354), whereas ablation requires destruction of viable tissue.

Therefore, the limits of the current therapeutic strategies for the treatment of cardiac arrhythmias based on re-entry mechanisms and in particular atrial fibrillation which include drug-based prolongation of the refractory period of cardiomyocytes and/or catheter-based techniques, suggest the need of further insights into involved arrhythmogenic mechanisms as well as emerging novel therapeutic concepts.

SUMMARY OF THE INVENTION

The present invention is related to the finding that globotriaosylceramide (Gb3) at concentrations in the nanomolar range directly interacts with membrane components and induces an enhanced conduction velocity along strands of cardiomyocytes in a concentration-dependent manner and without exhibiting cytotoxic effects. Re-entry mechanisms may be eliminated by different approaches such as increasing refractoriness (with subsequent prolongation of the QT interval), pursuing bidirectional block by blocking the sodium current, and finally, converting slow to more rapid conduction, thereby increasing the pathlength necessary for re-entrant events to occur (Lu et al., 2012, *J Cardiovasc Pharmacol*, 60:88-99; Savelieva et al., 2008, *Europace*, 10:647-65; Lau et cal., 2009, *Circulation*, 119:19-27; Takanari et al., 2011, *J Pharmacol Sci*, 115:15-2). Since converting slow to more rapid conduction is one of the three main ways by which re-entry mechanisms may be eliminated (by improving the probability of head-to-tail collision and thus annihilation of re-entry circuits), it is believed that the ability of Gb3 in enhancing the conduction velocity could display an anti-arrhythmic effect against impending arrhythmia based on re-entry mechanisms in general and would be useful in the protection against and treatment of cardiac arrhythmia, in particular atrial fibrillation. Although a very well-known principle, this approach has not succeed to be part of the current anti-arrhythmic armamentarium so far, since appropriate molecules have been missing or have failed to establish a reliable and reproducible conversion of flow to more rapid conduction or termination of arrhythmia. Therefore, based on its properties and existing observations, it is believed that glycosphingolipids selected from a globotriaosylceramide, glucosylceramide, or a sphingosine derivative of those would be useful in the protection against and treatment of cardiac arrhythmia, in particular atrial fibrillation.

A first aspect of the invention provides mono-, di-, and triglycosylceramides according to the invention for the prevention and/or treatment of cardiac arrhythmia based on reentry mechanisms, in particular atrial fibrillation.

Another aspect of the invention provides a pharmaceutical composition comprising one or more glycosphingolipids selected from a globotriaosylceramide, a glucosylceramide, a sphingosine derivative thereof, a mixture thereof and a pharmaceutically acceptable carrier, diluent or excipient thereof.

Another aspect of the invention provides use of a compound according to the invention for the preparation of a pharmaceutical composition, in particular for the prevention and/or treatment of cardiac arrhythmia based on reentry mechanisms, in particular atrial fibrillation. Another aspect of the invention is a method for preventing and/or treating a subject suffering from or at risk of suffering from cardiac arrhythmias based on reentry mechanisms, in particular atrial fibrillation, comprising administering a compound according to the invention or a pharmaceutical formulation thereof in a subject in need thereof.

DETAILED DESCRIPTION OF THE INVENTION

Figure 1:
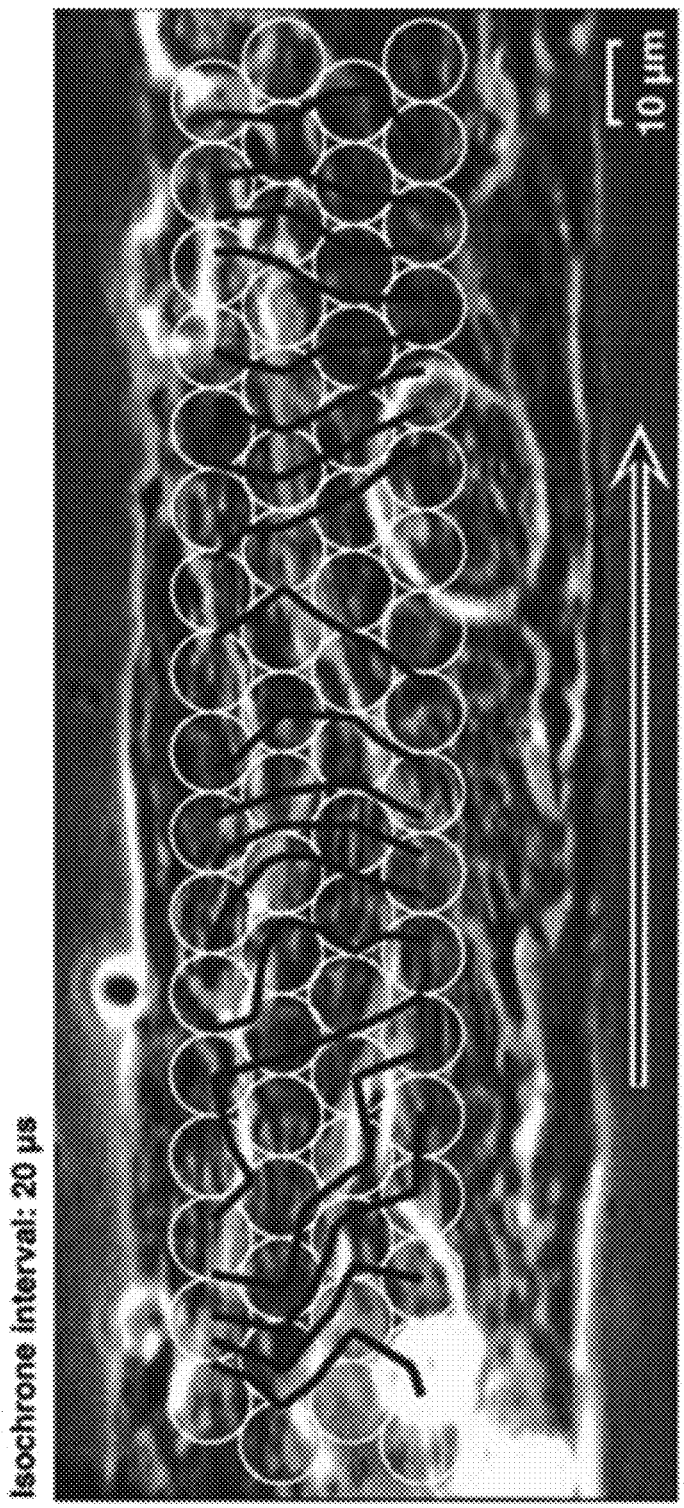
FIG. 1 represents a phase-contrast image of the preparation of tissue engineered strands of rat ventricular cardiomyocytes as described in Example 1, with white circles indicating the spatial arrangement of the photodetectors. The strand was stimulated on the left (arrow, direction of propagation) and isochrones of activation are shown as black lines.

The expression "cardiac arrhythmia" refers to an abnormal beating of the heart and comprises atrial fibrillation in particular and in more general terms any kind of atrial and/or ventricular arrhythmia based on reentry mechanisms.

The term "efficacy" of a treatment according to the invention can be measured based on time to effect (i.e. conversion of the arrhythmia into a normal rhythm), rate of successful conversion, rate of maintenance of normal rhythm after conversion, time to and rate of arrhythmia recurrence under treatment.

As used herein, "treatment" and "treating" and the like generally mean obtaining a desired pharmacological and physiological effect, in particular reducing the number of arrhythmic episodes and their duration as well as recurrence rates. The effect may be prophylactic in terms of preventing or partially preventing arrhythmia and/or may be therapeutic in terms of a partial or complete reduction of the arrhythmic events.

The term "subject" as used herein refers to mammals. For example, mammals contemplated by the present invention include human, primates, domesticated animals such as cattle, sheep, pigs, horses, laboratory rodents and the like.

The term "pharmaceutical composition" refers to preparations which are in such a form as to permit biological activity of the active ingredient(s) to be unequivocally effective and which contain no additional component which would be toxic to subjects to which the said composition would be administered.

Compounds of the Invention

Glycosphingolipids of the invention are mono-, di-, and triglycosylceramides selected from a globotriaosylceramide, a glucosylceramide, a galactosylceramide, a lactosylceramide and a sphingosine derivative of those or a mixture thereof.

According to a particular aspect, the glycosphingolipids are of Formula (I):

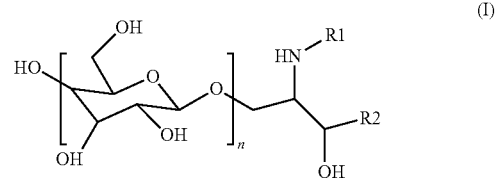

wherein R¹ is selected from a group —C(O)—R³ (ceramides) and H (sphingosines); R² is a group —C(H)=C(H)—R⁴, wherein R⁴ is an optionally substituted $C_{10}$-$C_{18}$ alkyl, in particular an optionally substituted $C_{13}$ alkyl; R³ is an optionally substituted $C_{15}$-$C_{23}$ alkyl (such a $C_{15}$-$C_{23}$ alkyl optionally substituted by hydroxyl), in particular an optionally substituted $C_{15}$-$C_{17}$ alkyl, more particularly an optionally substituted $C_{15}$ alkyl and n is an integer selected from 1, 2 and 3; as well as tautomers, geometrical isomers, optically active forms as enantiomers, diastereomers and racemate forms and pharmaceutically acceptable salts thereof or a mixture thereof.

According to a particular aspect, the glycosphingolipid of Formula (I) wherein n is 1.

According to a particular aspect, the glycosphingolipid of Formula (I) wherein n is 3.

According to a particular aspect, the glycosphingolipid of Formula (I) is globotriaosylceramide Gb3 or a pharmaceutically acceptable salt thereof.

According to another particular aspect, the glycosphingolipid of Formula (I) is sphingosine derivative of globotriaosylceramide Gb3, in particular Lyso-Gb3 or a pharmaceutically acceptable salt thereof.

According to a particular aspect, the glycosphingolipid of Formula (I) is glucosylceramide GL1 (β-glucosylceramide) or a pharmaceutically acceptable salt thereof.

According to another particular aspect, the glycosphingolipid of Formula (I) is sphingosine derivative of glucosylceramide GL1, in particular Lyso-GL1 or a pharmaceutically acceptable salt thereof.

Compounds of the invention are commercially available (Matreya, LLC 2178 High Tech Road, State College, PA 16803 USA) or can be synthesized as described in Nicolaou et al., 1990, *Carbohydr Res.*, 202:177-91.

Composition of the Invention

Pharmaceutical compositions of the invention can contain one or more compound according to the invention and a pharmaceutically acceptable carrier, diluent or excipient thereof.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

In another particular aspect, compositions according to the invention are adapted for delivery by single or multiple administrations.

According to a particular embodiment, compositions of the invention are veterinary compositions.

Further materials as well as formulation processing techniques and the like are set out in Part 5 of *Remington's "The Science and Practice of Pharmacy"*, 22$^{nd}$ Edition, 2012, University of the Sciences in Philadelphia, Lippincott Williams & Wilkins, which is incorporated herein by reference.

Mode of Administration

Compounds and compositions of this invention may be administered or delivered in any manner including, but not limited to, parenterally, orally, transdermally, intranasal or combinations thereof. Parenteral administration includes, but is not limited to, intra-intravenous, intra-arterial, intra-peritoneal, subcutaneous and intramuscular.

In another particular embodiment, a compound according to the invention is administered systemically by injection.

The dosage administered, as single or multiple doses, to an individual will vary depending upon a variety of factors, including pharmacokinetic properties, subject conditions and characteristics (sex, age, body weight, health, and size), extent of symptoms, concurrent treatments, frequency of treatment and the effect desired.

Combination

According to one embodiment of the invention, the compounds according to the invention and pharmaceutical formulations thereof can be administered alone or in combination with a co-agent useful in the prevention and/or treatment of a disease.

The invention encompasses the administration of a compound of the invention wherein the compound is administered to a subject prior to, simultaneously or sequentially with a therapeutic regimen or at least one co-agent. The compound according to the invention that is administered simultaneously with said at least one co-agent can be administered in the same or different compositions and in the same or different routes of administration.

Subjects

In an embodiment, subjects according to the invention are suffering from or at risk of suffering from cardiac arrhythmias, in particular based on reentry mechanisms.

In a further embodiment, subjects according to the invention are suffering from or at risk of suffering from atrial fibrillation.

Use According to the Invention

The compounds according to the invention are useful in the prevention and/or treatment of cardiac arrhythmias based on reentry mechanisms, in particular atrial fibrillation.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. The invention having been described, the following examples are presented by way of illustration, and not limitation.

EXAMPLES

The following abbreviations refer respectively to the definitions below:

HEPES (4-(2-hydroxyethyl)-1-piperazineethanesulfonic acid).

Example 1: Efficacy of a Globotriaosylceramide on the Conduction Velocity in Cardiomyocytes The effects of Gb3 on impulse propagation characteristics were investigated in tissue engineered strands of rat ventricular cardiomyocytes where impulse propagation was recorded using the voltage sensitive dye di-8-ANEPPS as described below.

Patterned Growth Cell Cultures

Cell cultures from neonatal rat heart (Wistar) exhibiting predefined growth patterns were prepared according to previously published photolithographic procedures (Rohr, *Circ Res.*, 1991, 68(1):114-130). The tissue structures used in this study consisted of linear cell strands (10 mm long; 50 to 300 mm wide) and strands exhibiting side-branches at defined intervals.

Optical Recording of Electrical Activation Patterns

Impulse propagation along the patterned preparations was followed optically using a fast voltage-sensitive dye (Rohr et al., 1994, *Biophys J.*, 67(3):1301-1315). In short, the preparations were stained for 3 to 4 minutes with 1 mL of the superfusion solution containing 135 mmol/L of the voltage-sensitive dye di-8-ANEPPS (Molecular Probes). The dye was excited by a short-arc xenon lamp driven by a low-ripple power supply (Optiquip). The light was, after passing a shutter (VS25S21 MO, Vincent Assoc), short-pass filtered (570 EFSP, Omega) and deflected toward the objective by means of a dichroic mirror (575 nm; Omega). Emitted fluorescence from the preparation was long-pass filtered (590 nm, Omega) and projected onto a 2-dimensional array of 379 optical fibers, which formed a hexagonal array (Rohr et al., 1998, *Biophys J.*, 75(2):1062-1075). From the entire array, ≤80 fibers were selected according to the shape of a given preparation and were connected to individual photodiodes. The resulting photocurrents were converted to voltages and amplified (typical overall gain of $2.5 \times 10^9$ V/A $f_0$=1.6 kHz). The conditioned signals were simultaneously sampled at 20 kHz/channel by a computer-based data acquisition system. Experiments were performed with a 20×, 0.75 numerical aperture (NA) objective (each detector monitored a circular area with a diameter of 50 um corresponding to 4 to 10 cells contributing to the signal) permitting assessment of activation along the preparations for distances up to 1 mm. The setup of the preparation is shown in FIG. 1.

Experimental Protocol

After mounting the preparations in the experimental chamber, control superfusion was started (Hanks' balanced salt solution (HBSS), containing (mmol/L) NaCl 137, KCl 5.4, $CaCl_2$ 1.3, $MgSO_4$ 0.8, $NaHCO_3$ 4.2, $KH_2PO_4$ 0.5, $NaH_2PO_4$ 0.3, and HEPES 10, which was titrated to pH 7.40 with NaOH). The preparations were stimulated with bipolar electrodes consisting of glass micropipettes (filling, HBSS with 1% agar) and a silver wire coiled around the shank of the electrode. The electrodes were attached to micromanipulators (DC-3K, Marzhauser) and placed at a sufficient distance from the measurement site (1 mm) to (1) avoid electronically mediated stimulation artifacts to distort the signal of interest and (2) permit propagation to reach steady-state conditions at the site of the measurement. Rectangular impulses (duration, 1 ms; 2-3 times threshold intensity) were delivered to the preparations at a basic cycle length of 500 ms by a stimulator (SD9, Grass Instruments) for at least 10 seconds before a given optical recording. All experiments were performed at a temperature of 36+/-0.4° C.

Exposure to Gb3

After 2 days in culture, preparations were exposed for another 24 hours to various concentrations of Gb3 ranging from concentration lower than, comparable to and higher than concentrations found in subjects with Fabry disease (Matreya, LLC 2178 High Tech Road, State College, PA 16803 USA) dissolved in normal cell culture medium.

Data Analysis

The raw data were analyzed by programming routines written in Interactive Data Language (IDL; Creaso). The data processing typically involved manual selection of the upstroke portions of the action potentials to omit any signal distortion due to motion artifacts occurring several milliseconds after the upstrokes. The data were digitally low-pass filtered and signal amplitudes obtained under control conditions were set to 100%. Only longitudinal velocities were determined, because the structure of the strands (mostly isotropic) and the stimulation arrangement did not permit a meaningful separation of longitudinal from oblique and transverse propagation in their proper sense (Spach et al., 1988, *Circ Res.*, 62(4):811-832; Spach et al., 1994, *J Cardiovasc Electrophysiol.*, 5(2):182-209).

Statistics

Figure 2:
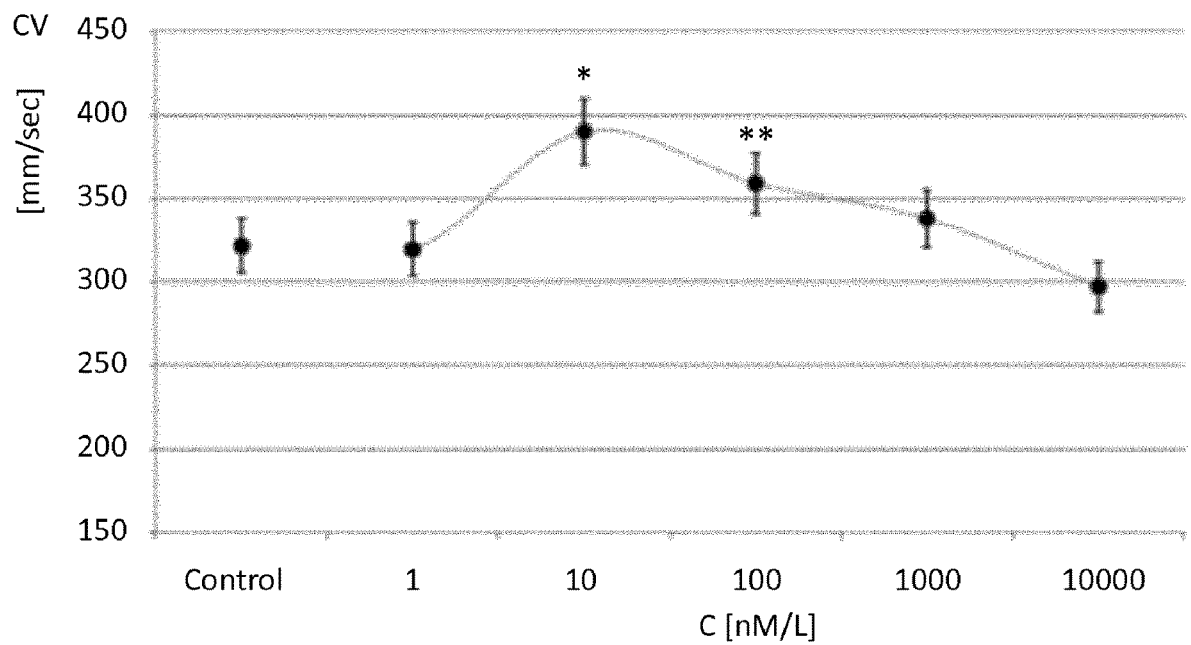
FIG. 2 represents the conduction velocity (CV) in cardiomyocytes versus the concentration (C) of Gb3 as described in Example 1.

Values (mean+/−SD) were compared using the Student t test (2-tailed, homo- or heteroscedastic where appropriate), and differences were considered significant at P<0.005 Conduction velocity (CV) along strands of cardiomyocytes was significantly enhanced at low Gb3 concentrations (in the nanomolar range). FIG. 2 shows a significant enhanced conduction velocity at concentrations of 10 nM to 100 nM of Gb3 with a gradual decrease in velocity measures with increasing concentrations. While control preparations conducted action potentials (APs) at a speed of 321.8±20.9 mm/sec (N=15), CVs in strands incubated with 10 nM Gb3 were increased by over 20% to 390.2±21.3 mm/sec (N=6, p<0.0001 versus control). At 100 nM and 1 µM, Gb3 concentration CV was still enhanced (358.8±20.3 mm/sec, p<0.005 vs control and 338.4±27.3 mm/sec, p=0.3 vs control) but showed a tendency to decline with increasing Gb3 concentrations. None of the concentrations of Gb3 used were associated with cytotoxic effects.

In order to investigate how Gb3 may affect impulse propagation in a model of discontinuous conduction, experiments were carried out with preparations having branched tissue architecture since branches were shown before to modulate CV dependent on inter-branch distances and branch lengths (Kucera et al., 1998, *Circ Res.*, 83(8):795-805) and therefore reflect physiological circumstances of cardiac tissue. A tissue design was chosen such as it reduces CV under control conditions to about 200 mm/sec and normalized multi-junction results to linear strands grown in parallel in the same branched tissue preparations. As expected, control multi-junction preparations displayed a substantially reduced CV when compared to linear strands (57.4±6.7%; N=28). However, when exposed to 10 nmol/L, Gb3 for 24 hrs, CV in multi-junction preparations was reduced to only 84.7±2.3% (N=25) of linear strands. Overall, this corresponds to a ~67% increase in CV in branched preparations treated with Gb3.

These data indicate that Gb3 seems to interact with cellular electrophysiological key components of conduction and enhances conduction velocity to a substantial degree in a concentration-dependent manner and without exhibiting cytotoxic effects.

The observation of an enhanced conduction velocity in the context of a cardiopathy is a rather exquisite phenomenon, as primary or secondary cardiac diseases for the most part come along with a conduction delay or block, representing key components of re-entrant arrhythmias. It is well known that slowing or block of conduction is based on a reduction of excitability (reduction of the sodium inward current INa), a decrease of gap junctional coupling and/or changes in the cellular architecture of cardiac tissue (Rohr et al., 1999, *Trends Cardiovasc Med.*, 9(7):173-179; Rohr et al., 1998, *Circ Res.*, 83(8):781-794). On the other hand, it is well established that reentry mechanisms may be eliminated by different approaches such as increasing refractoriness with subsequent prolongation of the QT interval, pursuing bidirectional block by blocking the sodium current, and finally, converting slow to more rapid conduction, thereby increasing the wavelength of the propagating action potential and, hence, reducing the potential for reentrant events to occur (Lu et al., 2012, *J Cardiovasc Pharmacol.*, 60(1):88-

99; Savelieva, 2008, *Europace*, 10(6):647-665; Lau et al., 2009, *Circulation*, 119(1):19-27). Along these lines, it has been shown that increasing the conduction velocity reduces incidence and maintenance of atrial fibrillation in dogs vulnerable to this arrhythmia. (Abdulmajeed et al., 2014; *Conf Proc IEEE Eng Med Biol Soc*. 2014; 2014:1067-70; Nattel et al., 2008, *Circulation: Arrhythmia and Electrophysiology*, 1(1):62-73).

Therefore, it is believed that mono-, di-, and triglycosylceramides of the invention such as globotriaosylceramides such as Gb3, glucosylceramides and sphingosine derivatives thereof may possess a protective and/or therapeutic role against impending and/or manifest arrhythmia based on reentry mechanisms.

Example 2: Cellular Effects of a Globotriaosylceramide of the Invention

A detailed characterization of the molecular mechanisms leading to the Gb3 induced increase of conduction velocities in cardiac tissue is carried out in bioengineered strands of cardiomyocytes as follows:

Gb-3 and lyso-Gb3 induced changes of the expression of the main determinants of cardiac conduction velocity (sodium channels, calcium channels, potassium channels, connexins) is analyzed at the message and protein level in isolated atrial and ventricular cardiomyocytes from Gb-3/lyso-Gb3 treated animals and in cardiomyocytes exposed in-vitro (primary cell culture).

For mRNA expression studies, total RNA is extracted from cardiomyocytes exposed to Gb3/lyso-Gb3, reverse transcribed to cDNA and expression of cDNAs coding for Nav1.5 (the main subunit of the voltage-gated fast sodium channel), connexin 40 and connexin 43 measured by real-time Polymerase Chain Reaction (TaqMan method). Expression of corresponding proteins is assessed by Western Blot of total cell extracts.

Immunocytochemistry on the same proteins is used to evaluate possible changes in the subcellular targeting of ion channels and connexins under the influence of a globotriaosylceramide of the invention such as Gb3 of lyso-Gb3.

Cardiomyocytes on glass coverslips are fixed with paraformaldehyde or glyoxal, permeabilized with Triton-X-100 and incubated overnight with antibodies against the protein of interest. Fluorophore-conjugated secondary antibodies are then be applied and confocal images of cardiomyocytes obtained with a Zeiss LSM800 confocal microscope. From these studies, insights into the kinetics of the effects of the compounds.

Example 3: Uptake and Metabolization Kinetics of a Glycosphingolipid of the Invention In order to determine whether glycosphingolipids of the invention are internalized in cardiomyocytes or act through a cell surface receptor, the following experiments are conducted. Cardiomyocytes are incubated with a fluorescently-labeled globotriaosylceramide of the invention (e.g. Gb3 or lyso-Gb3) for period of 1 hour to 24 hours. After extensive washing of the incubation medium, the cardiomyocytes are fixed with glyoxal and fluorescent images of the cardiomyocytes are acquired to determine whether the compound has been internalized by the cardiomyocytes as described in Richter et al., 2018, *EMBO J*. 2018; 37:139-159. Cell morphology and cell necrosis is monitored through the release of LDH in the culture medium.

Example 4: Cell-to-Cell Coupling in Cardiomyocytes Exposed to a Glycosphingolipid of the Invention In order to investigate the effect of a globotriaosylceramide of the invention (e.g. Gb3 or lyso-Gb3) on gap junctional coupling is investigated in cardiomyocyte cell pairs using dual whole cell recording, according to published protocols (Desplantez et al., 2004, *Pflugers Arch.*, 448:363-75) as follows since cell-to-cell coupling through gap junctions made mostly of connexin 43 (and connexin 40 in the atria) is another determinant of myocardial conduction velocity.

Atrial or ventricular cardiomyocytes are plated at densities adjusted to ensure the formation of cell pairs with reestablished cell-to-cell contact and coupling. Following exposure to the compound, both cardiomyocytes in a cell pair are patched in the "whole cell" configuration and the membrane potential of each cell clamped to the same value (0 mV). Thereafter the membrane potential V1 of one of cell 1 is stepped to a different value and the current recorded from cell 2 is the current through the junction between the two cells, from which the gap junction conductance can be calculated.

Example 5: Clinical Effects of a Globotriaosylceramide of the Invention

Interestingly, preliminary clinical observations have indicated a cycle length decrease and thus acceleration of arrhythmia mechanisms before spontaneous termination in patients with paroxysmal or persistent AF scheduled for radiofrequency ablation, thereby further supporting the usefulness of an agent increasing conduction velocity in those patients.

Therefore, an established cellular model of re-entrant excitation (van Middendorp et al., 2014, *Europace*, 16(8):1249-56; Courtemanche et al., 1998, *Am J Physiol Heart Circ Physiol.*, 275:H301-H321) is used to (1) assess Gb-3/lyso-Gb3 induced changes in critical pathlengths necessary for the induction of re-entry, with and without involvement of structural barriers to characterize the total length of interwave conduction block, (2) the number of fibrillation waves, and (3) the ratio of block to collision of fibrillation waves before and after exposure with Gb3.

The invention claimed is:
1. A method for treating a subject suffering from or at risk of suffering from cardiac arrhythmias based on reentry mechanisms, wherein treating is reducing the number of arrhythmic episodes and their duration as well as recurrence rates, said method comprising administering a globotriaosylceramide, or a sphingosine derivative thereof, a pharmaceutically acceptable salt thereof, a mixture thereof, or a pharmaceutical formulation thereof to a subject in need of treatment, wherein said globotriaosylceramide is Gb3:

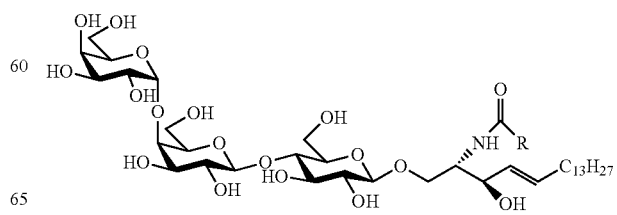

wherein R is selected from the group consisting of $C_{15}H_{31}$, $C_{19}H_{39}$, $C_{21}H_{43}$, $C_{23}H_{47}$ and $C_{23}H_{47}O$, or a pharmaceutically acceptable salt thereof.

2. The method according to claim 1, said globotriaosylceramide is a sphingosine derivative of globotriaosylceramide Gb3 or a pharmaceutically acceptable salt thereof.

3. The method according to claim 1, wherein said sphingosine derivative of globotriaosylceramide Gb3 is Lyso-Gb3:

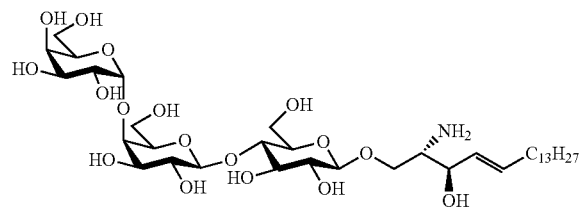

or a pharmaceutically acceptable salt thereof.

4. The method according to claim 1, wherein the cardiac arrhythmia is atrial fibrillation.

5. A pharmaceutical composition comprising Lyso-Gb3

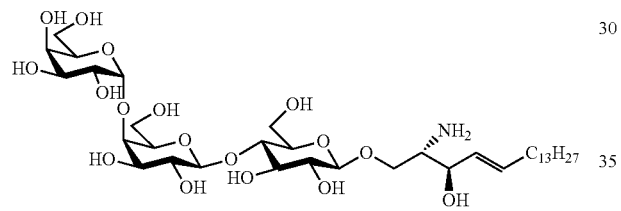

and a pharmaceutically acceptable carrier, diluent or excipient thereof.

6. The method according to claim 1, wherein the globotriaosylceramide, a sphingosine derivative thereof, a pharmaceutically acceptable salt thereof, a mixture thereof, or a pharmaceutical formulation thereof is administered to the subject in an amount that converts the cardiac arrhythmia into a normal rhythm.

7. The method according to claim 6, wherein the cardiac arrhythmia is atrial fibrillation and the globotriaosylceramide is Gb3

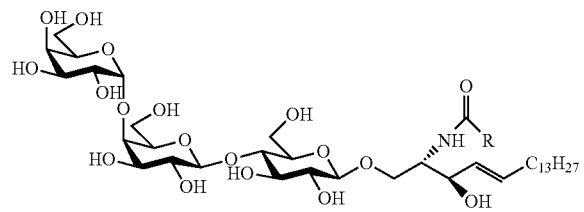

or a pharmaceutically acceptable salt thereof.

8. The method according to claim 6, wherein the cardiac arrhythmia is atrial fibrillation and the globotriaosylceramide is a sphingosine derivative of Gb3

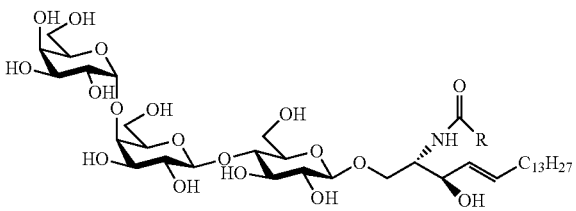

or a pharmaceutically acceptable salt thereof.

9. The method according to claim 6, wherein the cardiac arrhythmia is atrial fibrillation and the globotriaosylceramide is Lyso-Gb3

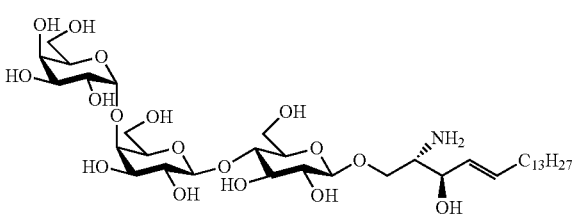

or a pharmaceutically acceptable salt thereof.

10. A method for converting a cardiac arrhythmia into a normal rhythm, said method comprising administering a globotriaosylceramide, or a sphingosine derivative thereof, a pharmaceutically acceptable salt thereof, a mixture thereof, or a pharmaceutical formulation thereof to a subject having a cardiac arrhythmia, wherein said globotriaosylceramide is Gb3:

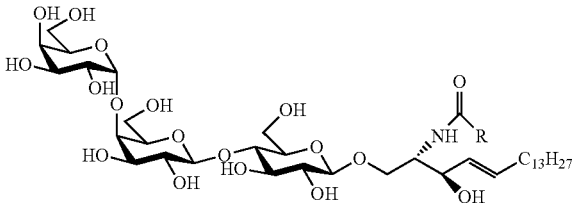

wherein R is selected from the group consisting of $C_{15}H_{31}$, $C_{19}H_{39}$, $C_{21}H_{43}$, $C_{23}H_{47}$ and $C_{23}H_{47}O$, or a pharmaceutically acceptable salt thereof.

11. The method according to claim 10, said globotriaosylceramide is a sphingosine derivative of globotriaosylceramide Gb3 or a pharmaceutically acceptable salt thereof.

12. The method according to claim 10, wherein said sphingosine derivative of globotriaosylceramide Gb3 is Lyso-Gb3:

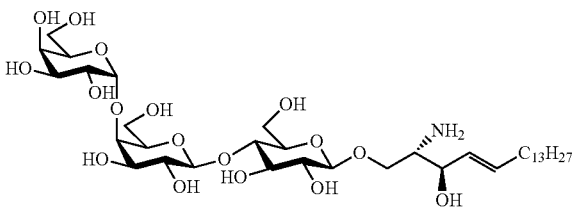

or a pharmaceutically acceptable salt thereof.

13. The method according to claim 10, wherein the cardiac arrhythmia is atrial fibrillation.

14. The method according to claim 13, wherein the cardiac arrhythmia is atrial fibrillation and the globotriaosylceramide is Gb3

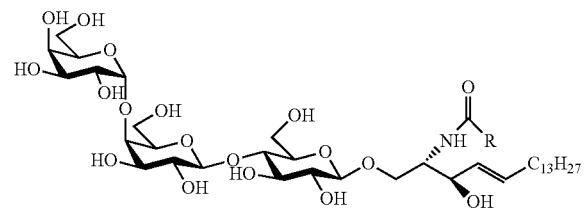

or a pharmaceutically acceptable salt thereof.

15. The method according to claim 13, wherein the cardiac arrhythmia is atrial fibrillation and the globotriaosylceramide is a sphingosine derivative of Gb3

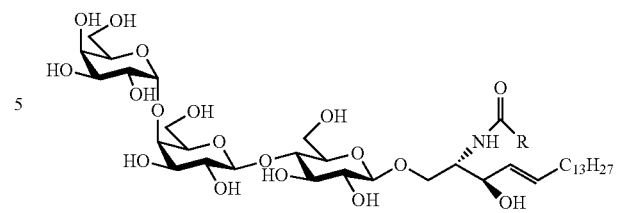

or a pharmaceutically acceptable salt thereof.

16. The method according to claim 13, wherein the cardiac arrhythmia is atrial fibrillation and the globotriaosylceramide is Lyso-Gb3

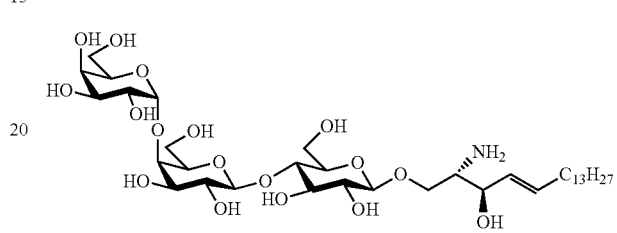

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 12,016,870 B2 | Page 1 of 1 |
| APPLICATION NO. | : 17/281276 | |
| DATED | : June 25, 2024 | |
| INVENTOR(S) | : Mehdi Namdar | |

It is certified that error appears in the above-identified patent and that said Letters Patent is hereby corrected as shown below:

In the Claims

<u>Column 11,</u>
Line 67, Claim 8, "derivative of Gb3" should read --derivative of globotriaosylceramide Gb3--.

<u>Column 12,</u>
Line 48, Claim 11, "claim 10, said" should read --claim 10, wherein said--.

Signed and Sealed this
Eleventh Day of March, 2025

Coke Morgan Stewart
*Acting Director of the United States Patent and Trademark Office*